United States Patent [19]

Campbell et al.

[11] 4,244,864

[45] Jan. 13, 1981

[54] POLY(6-OXY-2,2,4-TRIALKYL-1,2-DIHYDROQUINOLINE)ALKYLENE COMPOUNDS AS ANTIDEGRADANTS FOR RUBBER

[75] Inventors: Robert H. Campbell; Raleigh W. Wise; William A. Vaughn, all of Akron, Ohio

[73] Assignee: Monsanto Company, St. Louis, Mo.

[21] Appl. No.: 62,266

[22] Filed: Jul. 30, 1979

[51] Int. Cl.³ .................. C08K 5/34; C07D 215/14
[52] U.S. Cl. .................. 260/45.8 NW; 260/800; 546/166; 546/178
[58] Field of Search .................. 260/45.8 NW, 800; 546/178, 166

[56] References Cited

U.S. PATENT DOCUMENTS

| 2,165,623 | 7/1939 | Dunbrook et al. | 260/800 |
| 2,226,771 | 12/1940 | Ingram | 260/802 |
| 2,530,774 | 11/1950 | Kehe et al. | 260/283 |
| 2,947,720 | 8/1960 | Webb | 260/45.8 |
| 3,049,510 | 8/1962 | Harris | 260/45.8 |
| 3,244,683 | 4/1966 | Kline | 260/88.3 |
| 3,337,493 | 8/1967 | New et al. | 260/45.8 |

FOREIGN PATENT DOCUMENTS 40-3918   3/1965   Japan .................. 546/178

Primary Examiner—V. P. Hoke
Attorney, Agent, or Firm—Gordon B. Seward

[57] ABSTRACT

Vulcanizable or vulcanized diene elastomers containing stabilizing amounts of certain poly(6-oxy-2,2,4-trialkyl-1,2-dihydroquinoline)alkylene antidegradants show resistance to ozone attack. The antidegradants themselves are novel compounds.

14 Claims, No Drawings

POLY(6-OXY-2,2,4-TRIALKYL-1,2-DIHYDROQUINOLINE)ALKYLENE COMPOUNDS AS ANTIDEGRADANTS FOR RUBBER

BACKGROUND OF THE INVENTION

This invention relates to a novel class of antidegradant compounds and to vulcanized or vulcanizable diene elastomers containing stabilizing amounts thereof.

U.S. Pat. No. 2,165,623 discloses a class of 6-alkoxy-2,2,4-trialkyl-1,2-dihydroquinoline compounds shown to be effective as antioxidants or age retarding compounds in rubber.

SUMMARY OF THE INVENTION

A new class of compounds has now been found, corresponding to the formula:

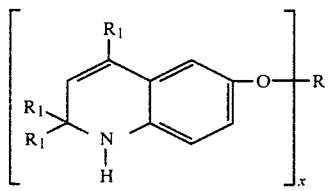

wherein the $R_1$s are the same or different alkyl radicals, R is a straight or branched chain alkenyl radical of from one to ten carbon atoms having a valence of x, and x is an integer of from two to four.

These compounds have been shown to have utility as antidegradants for vulcanizable diene rubber compounds, especially as antiozonants.

Synthesis of the compounds of the invention has been accomplished by condensing, under acidic conditions, a poly-4-aminophenoxy)alkylene, of the formula:

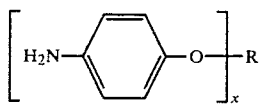

wherein R is an alkenyl radical of from one to ten carbon atoms having a valence of x, and x is an integer of from two to four, with a ketone of the formula:

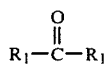

wherein the $R_1$s are the same or different lower alkyl radicals. One mole of the former compound is reacted with 2x moles of the ketone. The reaction products show very good activity as antidegradants, and especially antiozonants in vulcanizable diene rubber compounds.

Either the compounds or the reaction products defined above are very effective antidegradants for rubber. The reaction products may contain small amounts of unreacted poly(aminophenoxy) alkylene compounds or higher molecular weight products; however, these materials also seen to have antidegradant activity and, in any event, are generally not detrimental to rubber compounds containing them.

SPECIFIC EMBODIMENTS OF THE INVENTION

Examples of the novel compounds which fall within the general formula set forth first above include:
6,6'-(methylenedioxy) bis(1,2-dihydro-2,2,4-trimethylquinoline),
6,6'-(ethylene-1,2-dioxy) bis(1,2-dihydro-2,2,4-trimethylquinoline),
6,6'-(propylene-1,3-dioxy) bis(1,2-dihydro-2,2,4-trimethylquinoline),
6,6'-(butylene-1,4-dioxy) bis(1,2-dihydro-2,2,4-trimethylquinoline),
6,6'-(pentylene-1,5-dioxy) bis(1,2-dihydro-2,2,4-trimethylquinoline),
6,6'-(hexylene-1,6-dioxy) bis(1,2-dihydro-2,2,4-trimethylquinoline),
6,6'-(methylenedioxy) bis(1,2-dihydro-2,2-dimethyl-4-ethylquinoline),
6,6'-(ethylene-1,2-dioxy) bis(1,2-dihydro-2,2-dimethyl-4-ethylquinoline),
6,6'-(pentylene-1,5-dioxy) bis(1,2-dihydro-2,2-dimethyl-4-ethylquinoline),
6,6'-(ethylene-1,2-dioxy) bis(1,2-dihydro-2,2,4-triethylquinoline),
6,6'-(heptylene-1,7-dioxy) bis(1,2-dihydro-2,2,4-trimethylquinoline),
6,6'-(octylene-1,8-dioxy) bis(1,2-dihydro-2,2,4-trimethylquinoline),
6,6'-(2-ethyl-hexylene-1,3-dioxy) bis(1,2-dihydro-2,2,4-trimethylquinoline),
6,6,6''(ethylene-1,1,1-trimethoxy) tris(1,2-dihydro-2,2,4-trimethylquinoline),
6,6,6'',6'''(methylenetetramethoxy) tetrakis(1,2-dihydro-2,2,4-trimethylquinoline),
and the like. Of the above listed compounds, the 6,6'-(alkalenedioxy) bis(1,2-dihydro-2,2,4-trialkylquinoline) compounds are preferred.

The antidegradant reaction products which are effective can be produced by reacting one mole of a poly (4-aminophenoxy)alkylene compound such as:
bis(4-aminophenoxy)methane,
1,2-bis(4-aminophenoxy)ethane,
1,3-bis(4-aminophenoxy)propane,
1,4-bis(4-aminophenoxy)butane,
1,5-bis(4-aminophenoxy)pentane,
1,6-bis(4-aminophenoxy)hexane,
1,7-bis(4-aminophenoxy)heptane,
1,8-bis(4-aminophenoxy)octane,
1,10-bis(4-aminophenoxy)decane,
tris(4-aminophenoxy)methane,
1,1,1-tris(4-aminophenoxy)ethane,
tetrakis(4-aminophenoxy)methane,
and the like, with two moles of a dialkyl ketone for each molecule of nitrogen in the poly(4-aminophenoxy)alkylene compound.

Representative ketones which can be used include acetone, methyl ethyl ketone, methyl propyl ketone, methyl isopropyl ketone, diethyl ketone, methyl isobutyl ketone, methyl butyl ketone, ethyl propyl ketone, ethyl isopropyl ketone, ethyl isobutyl ketone, diisopropyl ketone, and the like. In general, ketones containing less than seven carbon atoms are preferred.

The poly(4-aminophenoxy) alkane compounds can be prepared in any convenient manner, such as by reacting one or more moles of para-nitrochlorobenzene with one mole of an alkyl polyol under basic conditions, and reducing the poly(4-nitrophenoxy) alkane thus formed to produce the poly(4-aminophenoxy) alkane. A number of poly(4-aminophenoxy) alkane compounds are commercially available.

While the novel compounds are preferably based on poly(4-aminophenoxy) alkanes, the amino group can also be in the 3 or 2 position on the benzene ring if desired.

In use, the antidegradants of the invention are incorporated into sulfur-vulcanizable diene rubber. Rubber containing more than 50% diene hydrocarbon is preferred. The preferred groups of rubber include natural rubber, styrene-butadiene copolymer rubber and the various stereospecific polymerized dienes; for example, cis-1,4-polybutadiene and cis-1,4-polyisoprene, and copolymers of styrene with isoprene or butadiene. The antidegradants are also useful in diene rubbers of low unsaturation such as butyl rubber and ethylene-propylene diene terpolymer rubber (EPDM). The optimum amount of the antidegradants to use will vary depending upon the particular formulation and the intended use of the rubber compound; but, in general, the amounts employed will usually fall within the range of 0.1 to 5% based on the rubber content of the compound.

Stereospecific rubbers are normally produced in solution or suspension in an organic solvent and it is important to add an antidegradant to the organic solvent composition immediately after polymerization has been completed because these rubbers deteriorate rapidly unless adequately protected from this point on. The antidegradants are also suited for addition to a rubber latex, for example, to protect the rubber phase of SBR rubber after coagulation and drying.

Rubber ozone resistance data for the product of this invention is obtained by a method published by Decker and Wise, "The Stress Releaxation Method for Measuring Ozone Cracking," *Rubber World*, April 1962, page 66. The equipment comprises an oven serving as an ozone cabinet filled with ozone generating equipment and racks for both static and dynamic testing. Static racks handle stocks at strains of 5, 10, 20, 30, and 40%. The dynamic rack is a reciprocal mechanism which imparts a 25% strain to the rubber test piece on movement of a top plate which moves vertically with respect to a stationary bottom plate. The mechanism is driven at a rate of 90 cycles per minute by a gear mounted on the outside of the cabinet. The test pieces are 2-inch (51 mm) long T-50 (ASTM D599-55) specimens died from standard stress strain test sheets (ASTM D15-57T). They are mounted by placing the ends in radial slots milled into the edges of circular plates of the racks. The tab ends fit into circumferential grooves machined into the outer surfaces of the plates.

The Stress Relaxation Method as identified above is based on the principle that the effective cross-sectional area of a small test piece of rubber is reduced by ozone cracking. The extent of cracking in a test piece is determined by measuring the forces required to extend the test piece 100% before and after exposure to ozone. The ozone concentration for the test is 25 parts ozone/100 million parts air. As the strip begins to crack, the number of stress supporting rubber chains decreases and the force required to extend the strip 100% is reduced. The ratio of this force to the original force is calculated at approximately 16-hour intervals of exposure to ozone. The graph of force vs. time is essentially a straight line and the elapsed time to reach 90%, 80%, and 70%, respectively, of the original force is determined from the graph. The capacity of the rubber to resist ozone attack is evaluated by a comparison of these determined times with times for suitable controls to reach a corresponding percent of the original force. Longer times indicate better ozone resistance in the rubber stock. The intermittent test comprises 2-hour cycles during which the specimens are exposed dynamically 15% of the time and are exposed statistically at 25% strain for the remaining 85% of the time.

EXAMPLE I

Into a suitable reactor equipped with an agitator, a condensor, a thermowell and facilities for heating and cooling were charged 45 grams (0.1844 moles) of 4,4'-(ethylenedioxy) dianiline, and 3.0 grams (0.0158 moles) of toluene sulfonic acid .$H_2O$. The reactor contents were heated to 160°–170° C., and acetone was added below the surface dropwise at a rate (about 24–30 drops per minute) so that the rate of acetone boiled off was almost equal to the rate of addition. The temperature was then maintained at 150°–160° C. After 10 hours (during which time 360 ml. of acetone was charged) all of the 4,4'-(ethylenedioxy) dianiline had apparently disappeared, and the reaction mass was cooled below about 90° C. To the reactor was added 75 ml. $CHCl_3$ to dissolve the reaction mass, and the resultant solution was transferred to a separatory funnel. There the solution was successively extracted with 30 ml. of 1.0 N NaOH in 30 ml. of water, 75 ml. of water, and finally, 100 ml. of water. The $CHCl_3$ was stripped off under 17 mmHg absolute pressure at 70° C. for 45 minutes, and the remaining product was transferred into a teflon-lined dish. Yield was 56 grams of "crude" product.

A portion (40 grams) of the "crude" product was dissolved in 150 ml. benzene and filtered at about 50° C. through a 0.5 $in^2$ super filtrol bed. The benzene was then stripped off under 17 mmHg (2.26 kPa) absolute pressure at 70° C., and the sample was taken off into another dish, and found to weigh about 32 grams. For further purification, 28 grams of the above product was dissolved in 60 ml. benzene by warming to 55° C. Then 90 ml. of hexane was added slowly while stirring. After the mixture was cooled to 30° C., two layers formed. The upper layer was decanted and stripped under 17 mmHg pressure at 70° C. then recovered and weighed. The final yield was 13 grams of "purified" product.

EXAMPLE II

The procedure of Example I was repeated, except that 1,5-bis (4-aminophenoxy)pentane was substituted for the 4,4'-(ethylenedioxy) dianiline. The product, 6,6'-(pentylene dioxy) bis(1,2-dihydro-2,2,4-trimethylquinoline) was purified in the same manner.

Analyses of the reaction products were performed by Gel Permeation Chromatography. Assays were determined by measuring the area percent of the desired compound. The remainder of the product was intermediates and higher molecular weight materials, which appeared to function as an antidegradant, to some extent. Depending on the degree of purification or isolation performed, assays ranged from about 45% up to 95% of the total product.

Evaluation of the various products of differing assays was performed by incorporating them into rubber compounds and evaluating their antidegradant activity. The evaluations are set forth in the following examples. The compound 6,6'-(ethylenedioxy) bis(1,2-dihydro-2,2,4-trimethylquinoline) is abbreviated to "EDBDT." The compound 6,6'-(pentylenedioxy) bis(1,2-dihydro-2,2,4-trimethylquinoline) is identified as "PDBDT."

Samples were mixed, cured 28 minutes at 153° C., and evaluated as shown in Table II, following.

TABLE II

| Component, Stock | 1 | 2 | 3 | 4 | 5 | 6 | 7 | 8 | 9 | 10 | 11 | 12 |
|---|---|---|---|---|---|---|---|---|---|---|---|---|
| Masterbatch | 164.0 | → | → | → | → | → | → | → | → | → | → | → |
| Sulfur | 2.0 | → | → | → | → | → | → | → | → | → | → | → |
| Accelerator | 1.0 | → | → | → | → | → | → | → | → | → | → | → |
| S-13 | — | 2.5 | | | | | 2.5 | | 2.5 | | | |
| S-IP | | | 2.5 | | | | | | | 2.5 | | |
| S-AW | | | | 2.5 | | | | | | | 2.5 | |
| E-67 | | | | | | 2.5 | | | | | | 2.5 |
| E-45 | | | | | 2.5 | | | | | | | 2.5 |
| Wax | | | | | | | | 2.5 | 2.5 | 2.5 | 2.5 | 2.5 |
| Stress/Strain Unaged | | | | | | | | | | | | |
| 300% Modulus, MPa | 7.8 | 6.7 | 6.8 | 6.1 | 6.4 | 7.0 | 6.7 | 6.0 | 5.8 | 4.9 | 5.6 | 6.1 |
| Ultimate Tensile, MPa | 23.4 | 21.2 | 20.2 | 22.6 | 22.4 | 21.4 | 21.4 | 21.4 | 21.9 | 20.5 | 21.1 | 22.0 |
| Ultimate Elongation, % | 590 | 602 | 587 | 656 | 658 | 595 | 618 | 644 | 647 | 696 | 671 | 656 |
| Shore "A" Hardness | 53 | 50 | 50 | 50 | 51 | 54 | 50 | 48 | 48 | 48 | 50 | 54 |
| Aged 48 Hrs. @100° C. in Al. Block | | | | | | | | | | | | |
| 300% Modulus, MPa | — | 10.1 | 10.2 | 9.0 | 11.2 | 11.6 | — | 9.8 | 9.5 | 8.2 | 9.9 | 10.1 |
| Ultimate Tensile, MPa | 7.5 | 13.3 | 16.5 | 14.0 | 15.0 | 16.2 | 7.4 | 16.0 | 16.5 | 14.6 | 14.9 | 15.9 |
| Ultimate Elongation, % | 249 | 361 | 409 | 412 | 373 | 383 | 263 | 427 | 453 | 451 | 396 | 418 |
| Shore "A" Hardness | 60 | 65 | 65 | 62 | 64 | 67 | 61 | 71 | 62 | 60 | 62 | 69 |
| % Retention of Ult. Tensile | 32 | 63 | 82 | 62 | 67 | 76 | 34 | 75 | 76 | 72 | 71 | 72 |
| Aged 72 Hrs. @100° C. | | | | | | | | | | | | |
| 300% Modulus, MPa | — | — | — | — | — | — | — | — | 11.9 | — | — | 11.7 |
| Ultimate Tensile, MPa | 5.1 | 10.6 | 12.0 | 8.8 | 11.2 | 11.0 | 5.3 | 11.0 | 12.3 | 8.5 | 10.6 | 12.5 |
| Ultimate Elongation, % | 176 | 279 | 291 | 279 | 282 | 275 | 174 | 292 | 306 | 296 | 294 | 314 |
| Shore "A" Hardness | 64 | 64 | 66 | 70 | 69 | 74 | 68 | 65 | 63 | 63 | 69 | 64 |
| % Retention of Ult. Tensile | 22 | 50 | 60 | 39 | 50 | 52 | 25 | 52 | 56 | 42 | 50 | 57 |

EXAMPLE III

The products of Example I were compared with standard antidegradants in a rubber compound of the type used in the sidewalls of radial tires:

| | Weight, Parts |
|---|---|
| Banbury Masterbatch | |
| Natural Rubber | 50.0 |
| Cis-1,4-polybutadiene | 50.0 |
| Carbon Black | 50.0 |
| Processing Oil | 10.0 |
| Zinc Oxide | 3.0 |
| Stearic Acid | 1.0 |
| | 164.0 |
| Mill Mix | |
| Masterbatch | 164.0 |
| Sulfur | 2.0 |
| Accelerator | 1.0 |
| Wax | Variable |
| Antidegradant | 2.5 |

The accelerator used was N-tertiary-butyl-2-mercaptobenzothiazolesulfenamide. The antidegradants compared are identified in the following Table I.

TABLE I

| Code | Compound |
|---|---|
| S-13 | N-1,3-dimethylbutyl-N'-phenyl-p-phenylenediamine |
| S-IP | N-isopropyl-N'-phenyl-p-phenylene diamine |
| S-AW | 6-ethoxy-1,2-dihydro-2,2,4-trimethylquinoline |
| E-67 | EDBDT, 67% assay |
| E-45 | EDBDT, 45% assay |

From the stress/strain data it appears that the EDBDT materials are almost as good antioxidants as the two PPD compounds (S-13 and S-IP) and better than S-AW, whether or not wax is present.

To evaluate the ozone protecting qualities of the antidegradants, they were tested in the same rubber formulation according to the Stress Relaxation Method described supra, with and without wax. The stocks containing wax are compared in the following Table III.

TABLE III

| | Antidegradant | | | | | |
|---|---|---|---|---|---|---|
| | None | S-13 | S-IP | S-AW | E-67 | E-45 |
| T-50 Ozone Test Unaged | | | | | | |
| Dynamic, 32 Hrs. Exposure, f/f$_o$ | Broke | 87 | 94 | 70 | 80 | 92 |
| Intermittent, 48 Hrs. Exposure, f/f$_o$ | Broke | 88 | 92 | 71 | 84 | 91 |
| Static, 128 Hrs. Exposure, f/f$_o$ | Broke | 98 | 100 | 78 | 99 | 96 |
| Aged 24 Hrs. @ 100° C. | | | | | | |
| Dynamic, 16 Hrs Exposure, f/f$_o$ | 32 | 86 | 87 | 49 | 77 | 65 |
| Intermittent, 16 Hrs. Exposure, f/f$_o$ | Broke | 97 | 91 | 54 | 87 | 82 |
| Static, 48 Hrs. Exposure, f/f$_o$ | Broke | 98 | 99 | 98 | 95 | 92 |
| TOTAL f/f$_o$ | | 554 | 563 | 420 | 522 | 518 |
| TOTAL f/f$_o$ Normalized to S-13 | | 100 | 102 | 76 | 94 | 94 |

Stocks with no wax are compared in Table IV, following.

TABLE IV

| | Antidegradant | | | | | |
|---|---|---|---|---|---|---|
| | None | S-13 | S-IP | S-AW | E-67 | E-45 |
| T-50 Ozone Test | | | | | | |
| Unaged | | | | | | |
| Dynamic, Hrs. to 70% (f/f$_o$) | 16 | 108 | 118 | 72 | 70 | 45 |
| Intermittent, Hrs. to 70% (f/f$_o$) | 10 | 70 | 110 | 47 | 15 | 14 |
| Static, Hrs. to 70% (f/f$_o$) | 10 | 48 | 96 | 48 | 10 | 9 |
| Aged | | | | | | |
| Dynamic, Hrs. to 70% (f/f$_o$) | 28 | 78 | 78 | 32 | 38 | 44 |
| Intermittent, Hrs. to 70% (f/f$_o$) | 12 | 36 | 46 | 14 | 12 | 12 |
| Static, Hrs. to 70% (f/f$_o$) | 12 | 16 | 24 | 13 | 12 | 12 |
| Total Hrs. | 88 | 356 | 472 | 226 | 157 | 136 |
| Total Hrs. Normalized to S-13 | 25 | 100 | 132 | 63 | 44 | 38 |

From the ozone testing data it is seen that the antidegradants of the invention are superior to S-AW when the rubber stock contains wax; however, without wax they are not as effective as S-AW. The stocks containing S-13 and S-IP gave better ozone performance with or without wax.

Since the staining characteristics of antidegradants can be important when rubber compounds come in contact with, for example, painted surfaces, the antidegradants of the invention were compared with other commercial antidegradants for migration staining, using ANSI/ASTM test D925-76. Using the same compound formulation set forth in Table II above, the behavior of the antidegradants was compared after four days contact at 80° C. The migration staining characteristics were visually rated on a scale of zero to five, zero being the least staining. Results of the test are set forth in Table V, following.

TABLE V

| Sample | Antidegradant | Wax | Rating |
|---|---|---|---|
| 1 | None | No | 0 |
| 2 | S-13 | No | 5 |
| 3 | S-IP | No | 5 |
| 4 | S-AW | No | 4 |
| 5 | EDBDT-67 | No | 2 |
| 6 | EDBDT-45 | No | 2 |
| 7 | None | Yes | 0 |
| 8 | S-13 | Yes | 5 |
| 9 | S-IP | Yes | 5 |
| 10 | S-AW | Yes | 5 |
| 11 | EDBDT-67 | Yes | 2 |
| 12 | EDBDT-45 | Yes | 2 |

The migration staining results show EDBDT to be less staining than any of the other commercial antidegradants.

EXAMPLE IV

The antidegradants of the invention were compared to known commercial antidegradants in a typical tire white sidewall compound, having the following formulation:

| | Weight, Parts |
|---|---|
| Banbury Masterbatch | |
| Natural Rubber (pale crepe) | 70.0 |
| SBR 1502 | 30.0 |
| Titanium Dioxide | 40.0 |
| Clay | 15.0 |
| Zinc Oxide | 20.0 |
| Stearic Acid | 1.5 |
| Wax | 2.5 |
| | 179.0 |
| Mill Mix | |
| Masterbatch | 179.0 |
| Insoluble Sulfur | 2.0 |
| Accelerator | 0.8 |
| TOTAL | 181.8 |

The accelerator was the same as that used in Example III. The antidegradants compared are identified in Table VI, following.

TABLE VI

| Code | Compound |
|---|---|
| TBTU | Tributyl Thiourea |
| 2246 | 2,2'-Methylene-bis-(4-Methyl-6-t-butylphenol) |
| S-13 | Same as in Table I |
| S-AW | Same as in Table I |
| E-67 | Same as in Table I |
| P-88 | PDBDT, 88% assay |

Samples were mixed, cured 28 minutes at 153° C., and evaluated as shown in Table VII, following.

TABLE VII

| Component | 1 | 2 | 3 | 4 | 5 | 6 | 7 |
|---|---|---|---|---|---|---|---|
| Masterbatch | 181.8 | → | → | → | → | → | → |
| TBTU | — | 2.0 | — | — | — | — | — |
| 2246 | — | — | 2.0 | — | — | — | — |
| S-13 | — | — | — | 2.0 | — | — | — |
| S-AW | — | — | — | — | 2.0 | — | — |
| E-67 | — | — | — | — | — | 2.0 | — |
| P-88 | — | — | — | — | — | — | 2.0 |
| Stress/Strain | | | | | | | |
| Unaged | | | | | | | |
| 300% Modulus, MPa | 4.3 | 4.7 | 4.4 | 4.4 | 4.6 | 4.6 | 4.7 |
| Ult. Tensile, MPa | 22.0 | 21.9 | 22.0 | 20.8 | 21.4 | 19.9 | 20.3 |
| Ult. Elongation, % | 638 | 597 | 618 | 592 | 571 | 568 | 587 |
| Shore "A" Hardness | 50 | 54 | 51 | 51 | 50 | 51 | 51 |
| Aged 48 Hrs. @ 100° C. | | | | | | | |
| 300% Modulus, MPa | 5.0 | 5.0 | 6.0 | 5.0 | 5.8 | 6.4 | 5.9 |
| Ult. Tensile, MPa | 12.8 | 14.1 | 20.2 | 20.4 | 21.9 | 16.7 | 18.1 |
| Ult. Elongation, % | 492 | 499 | 522 | 539 | 557 | 487 | 509 |
| Shore "A" Hardness | 54 | 53 | 57 | 57 | 57 | 57 | 57 |

TABLE VII-continued

| Component | 1 | 2 | 3 | 4 | 5 | 6 | 7 |
|---|---|---|---|---|---|---|---|
| Ult. Tensile, % Retention | 58.2 | 64.4 | 91.5 | 97.9 | 102.3 | 86.0 | 89.0 |

The stress/strain data indicate that the antidegradants of the invention were better antioxidants than TBTU, but not quite as good as 2246, S-13 and S-AW.

The antidegradants of the invention were compared with S-13 and S-AW for antiozonant activity in the same rubber formulations as above, using the Stress Relaxation Test. Results are summarized in Table VIII following. Rather than setting forth the hours required to reach 70% of original tensile strength, this table shows the percentage of the original tensile strength retained at specific times, i.e., 16, 32, and 64 hours.

TABLE VIII

| | None | S-13 | S-AW | E-67 | P-88 |
|---|---|---|---|---|---|
| Ozone T-50 Data | | | | | |
| Unaged, 25 pphm O₃ | | | | | |
| Dynamic % @ 32 Hrs. | — | 89 | 60 | 73 | 73 |
| Intermittent % @ 64 Hrs. | — | 90 | 75 | 86 | 89 |
| Static % @ 64 Hrs. | — | 99 | 97 | 96 | 95 |
| Mean Normalized to 100% for S-13 | | 100.0 | 83.4 | 91.7 | 92.4 |
| Aged, 25 pphm O₃ | | | | | |
| Dynamic % @ 16 Hrs. | 55 | 92 | 80 | 83 | 82 |
| Intermittent % @ 48 Hrs. | 46 | 91 | 66 | 80 | 79 |
| Static % @ 64 Hrs. | — | 96 | 72 | 75 | 74 |
| Mean | 50.5 | 93 | 72.7 | 79.3 | 78.3 |
| Normalized to 100% for S-13 | 54.3 | 100.0 | 78.2 | 85.3 | 84.2 |

The ozone data indicates that E-67 and P-88 have essentially the same activity as antiozonants. Both were better than S-AW, but not as good as S-13 as antiozonants.

The migration staining characteristics of the antidegradants of the invention were compared with the commercial antidegradants, in similar manner as the tests set forth in Example III, supra. The same rating method was also employed. Test results are shown in Table IX, following.

TABLE IX

| Sample | Antidegradant | Rating |
|---|---|---|
| 1 | None | 0 |
| 2 | TBTU | 0 |
| 3 | 2246 | 0 to trace |
| 4 | S-13 | 5 |
| 5 | S-AW | 3 |
| 6 | E-67 | 2+ |

TABLE IX-continued

| Sample | Antidegradant | Rating |
|---|---|---|
| 7 | P-88 | 1 |

The migration staining results indicate that E-67 and P-88 were superior to S-13 and S-AW, but not as good as either TBTU or 2246.

EXAMPLE V

The antidegradant activity of the compounds and reaction products of the invention was studied in a typical SBR black sidewall compound. Antioxidant and antiozonant activity was compared with known commercial materials. The following formula was used:

| | Weight, Parts |
|---|---|
| Masterbatch | |
| SBR-1712 | 96.0* |
| Cis-1,4-polybutadiene | 30.0 |
| Carbon Black | 50.0 |
| Zinc Oxide | 3.0 |
| Stearic Acid | 1.0 |
| Wax | 2.5 |
| | 182.5 |
| Mill Mix | |
| Masterbatch | 182.5 |
| Sulfur | 2.2 |
| Accelerator | 1.2 |
| TOTAL | 185.9 |

*contains 70 parts SBR, 26 parts oil

The accelerator was the same as that used in Examples III and IV, supra. The antidegradants compared are identified in Table X, following.

TABLE X

| Code | Compound |
|---|---|
| S-13 | Same as in Table I |
| S-AW | Same as in Table I |
| E-84 | EDBDT, 84% Assay |
| E-44 | EDBDT, 44% Assay |
| P-88 | PDBDT, 88% Assay |
| P-58 | PDBDT, 58% Assay |

Samples were mixed, and specimens cured to 28 minutes at 153° C., and evaluated as shown in Table XI, following.

TABLE XI

| Component | 1 | 2 | 3 | 4 | 5 | 6 | 7 |
|---|---|---|---|---|---|---|---|
| Masterbatch | 185.9 | → | → | → | → | → | → |
| S-13 | | 2.5 | | | | | |
| S-AW | | | 2.5 | | | | |
| E-84 | | | | 2.5 | | | |
| E-44 | | | | | 2.5 | | |
| P-88 | | | | | | 2.5 | |
| P-58 | | | | | | | 2.5 |
| Stress/Strain (Unaged) | | | | | | | |
| 100% Modulus, MPa | 1.7 | 1.7 | 1.7 | 1.8 | 1.7 | 1.6 | 1.7 |
| 300% Modulus, MPa | 9.5 | 9.1 | 8.9 | 9.1 | 9.0 | 8.8 | 9.1 |
| Ult. Tensile, MPa | 18.3 | 18.0 | 20.2 | 18.1 | 18.9 | 19.8 | 19.3 |
| Ult. Elongation, % | 455 | 461 | 517 | 465 | 475 | 469 | 438 |
| Shore "A" Hardness | 55 | 55 | 57 | 60 | 60 | 55 | 53 |

TABLE XI-continued

| Component | 1 | 2 | 3 | 4 | 5 | 6 | 7 |
|---|---|---|---|---|---|---|---|
| Stress/Strain (Aged 72 Hrs. @ 100° C.) | | | | | | | |
| 100% Modulus, MPa | 2.9 | 2.5 | 2.5 | 2.6 | 3.0 | 2.6 | 2.8 |
| 300% Modulus, MPa | — | 13.3 | 12.5 | 13.6 | 13.8 | 13.6 | 14.5 |
| Ult. Tensile, MPa | 14.4 | 15.1 | 15.2 | 14.1 | 15.7 | 14.4 | 15.0 |
| Ult. Elongation, % | 280 | 313 | 346 | 308 | 330 | 299 | 250 |
| Shore "A" Hardness | 66 | 65 | 66 | 64 | 64 | 66 | 68 |

The stress/strain data in Table IX, supra, show again that the antidegradants of the invention were roughly equivalents to each other, and had approximately the same antioxidant activity as the commercial compounds.

The same stocks were compared for ozone resistance as in Examples III and IV, with the results as set forth in Table XII, following.

TABLE XII

| Material | Control | S-13 | S-AW | E-84 | E-44 | P-88 | P-58 |
|---|---|---|---|---|---|---|---|
| Stock No. | 1 | 2 | 3 | 4 | 5 | 6 | 7 |
| Unaged Test, Total Hrs. | 68 | 201 | 130 | 164 | 132 | 137 | 149 |
| Aged 24 Hrs. @ 100° C., Total Hrs. | 53 | 142 | 92 | 104 | 96 | 97 | 105 |
| Overall Rating based on S-13 = 100% | 35 | 100 | 65 | 78 | 67 | 68 | 74 |

The ozone test data indicate, again, that the antidegradants of the invention show better antiozonant activity than S-AW, although not as good as S-13.

Although the invention has been illustrated by typical examples, it is not limited thereto. Changes and modifications of the examples of the invention herein chosen for purposes of disclosure can be made which do not constitute departure from the spirit and scope of the invention.

We claim:

1. A compound of the formula:

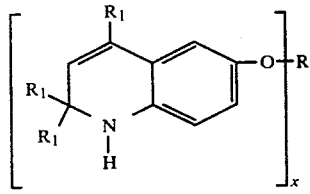

wherein the $R_1$'s are the same or different lower alkyl radicals, R is a straight or branched chain alkenyl radical of from one to ten carbon atoms, having a valence of x, and x is an integer of from two to four.

2. A compound according to claim 1 wherein the $R_1$'s are all methyl.

3. A compound according to claim 1 wherein the $R_1$'s are mixed methyl and ethyl.

4. A compound according to claim 1 wherein R is ethylene.

5. A compound according to claim 1 wherein R is pentylene.

6. 6,6'-(ethylene-1,2-dioxy)bis(1,2-dihydro-2,2,4-trimethylquinoline).

7. 6,6'-(pentylene-1,5-dioxy)bis(1,2-dihydro-2,2,4-trimethylquinoline).

8. Vulcanizable diene rubber having incorporated therein a stabilizing amount of the compound of claim 1.

9. The product of the reaction of substantially x moles of a compound of the formula:

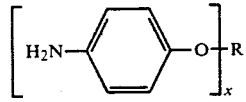

wherein R is a straight or branched chain alkenyl radical of frome one to ten carbon atoms, having a valence of x, and x is an integer of from two to four, with 2x moles of a ketone of the formula:

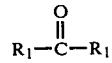

wherein the $R_1$'s are the same or different lower alkyl radicals.

10. The product of claim 9 wherein R is ethylene.
11. The product of claim 9 wherein R is pentylene.
12. The product of claim 9 wherein x is two.
13. The product of claim 9 wherein both $R_1$'s are methyl.
14. Vulcanizable diene rubber containing a stabilizing amount of the reaction product defined in claim 9.

* * * * *